US010251953B2

(12) United States Patent
Passlick-Deetjen et al.

(10) Patent No.: US 10,251,953 B2
(45) Date of Patent: Apr. 9, 2019

(54) PERITONEAL DIALYSIS SOLUTION

(75) Inventors: Jutta Passlick-Deetjen, Giessen (DE); Thomas P. Schaub, Bad Homburg (DE); Georg Topp, Laubach (DE)

(73) Assignee: Fresenius Medical Deutschland GMBH, Bad Homburg (DE)

(*) Notice: Subject to any disclaimer, the term of this patent is extended or adjusted under 35 U.S.C. 154(b) by 1622 days.

(21) Appl. No.: 11/596,181

(22) PCT Filed: May 12, 2005

(86) PCT No.: PCT/EP2005/005192
§ 371 (c)(1),
(2), (4) Date: Nov. 13, 2006

(87) PCT Pub. No.: WO2005/110442
PCT Pub. Date: Nov. 24, 2005

(65) Prior Publication Data
US 2007/0237835 A1    Oct. 11, 2007

(30) Foreign Application Priority Data

May 13, 2004  (DE) .................. 10 2004 023 828

(51) Int. Cl.
*A61K 33/14*     (2006.01)
*A61K 9/08*      (2006.01)
*A61M 1/28*      (2006.01)
*A61K 45/06*     (2006.01)
*A61K 31/7004*   (2006.01)

(52) U.S. Cl.
CPC .......... *A61K 45/06* (2013.01); *A61K 31/7004* (2013.01); *A61K 33/14* (2013.01); *A61M 1/287* (2013.01)

(58) Field of Classification Search
None
See application file for complete search history.

(56) References Cited

U.S. PATENT DOCUMENTS

| 5,346,472 A | 9/1994 | Keshaviah et al. |
| 5,589,197 A | 12/1996 | Shockley et al. |
| 5,629,025 A | 5/1997 | Shockley et al. |
| 5,631,025 A | 5/1997 | Shockley et al. |
| 6,277,815 B1 | 8/2001 | Knerr |
| 6,309,673 B1* | 10/2001 | Duponchelle et al. ........ 424/717 |
| 6,689,393 B1 | 2/2004 | Knerr |
| 7,011,855 B2 | 3/2006 | Martis et al. |
| 2002/0077580 A1 | 6/2002 | Tobe |
| 2003/0138501 A1* | 7/2003 | Elisabettini et al. ......... 424/717 |
| 2004/0129638 A1 | 7/2004 | Chang et al. |

FOREIGN PATENT DOCUMENTS

| DE | 694 04 805 T2 | 3/1998 |
| DE | 197 48 290 A1 | 5/1999 |
| DE | 199 12 850 A1 | 9/2000 |
| DE | 695 27 923 T2 | 4/2003 |
| EP | 0 602 585 A2 | 6/1994 |
| EP | 0 935 967 A2 | 8/1999 |
| EP | 1 038 552 A3 | 9/2000 |
| JP | 2000 037452 A | 2/2000 |
| WO | WO 00/64456 | 11/2000 |

OTHER PUBLICATIONS

Vande Walle J. et al., "Advantages of $HCO_3$ Solution with Low Sodium Concentration Over Standard Lactate Solutions for Acute Peritoneal Dialysis", Advances in Peritoneal Dialysis, vol. 13, pp. 179-182, 1997.
Nakayama, M., et al., "Anti-hypertensive Effect on Low Na Concentration (120 mEq/l) Solution for CAPD Patients", Clinical Nephrology, vol. 41, No. 6, pp. 357-363, 1994.

* cited by examiner

*Primary Examiner* — Hasan S Ahmed
*Assistant Examiner* — Frank Choi
(74) *Attorney, Agent, or Firm* — Kilyk & Bowersox, P.L.L.C.

(57) ABSTRACT

The present invention relates to a solution for peritoneal dialysis consisting of one or more separate solutions. A treatment free of side-effects with a simultaneous lowering of blood pressure can be achieved in that the solution contains sodium ions in a concentration in the region from 121 to 129 mmol/l, preferably at 125 mmol/l. The invention furthermore relates to a double-chambered pouch having a peritoneal dialysis solution consisting of two separate solutions which consists of a plastic pouch in which a first chamber with the first separate solution and a second chamber with the second separate solution are arranged adjacent to one another, with both chambers being separated from one another by a weld seam dimensioned such that it opens on pressure onto one of the chambers filled with liquid so that the content of the two chambers can be mixed with one another.

5 Claims, No Drawings

PERITONEAL DIALYSIS SOLUTION

This is a nationalization of PCT/EP05/005192 filed May 12, 2005 and published in German.

The invention relates to a solution for peritoneal dialysis in accordance with the preamble of claim 1.

Electrolytes are generally contained in a peritoneal dialysis solution in addition to a buffer system and an osmotic agent, said electrolytes typically being calcium salts, sodium salts and magnesium salts which are frequently used in the form of chlorides.

During the dialysis treatment, there is a transfer of numerous blood components, inter alia of sodium ions, from the blood of the patient to the dialysate via the peritoneum. The amount of the sodium removed from the blood in this manner depends among other things on the concentration gradient of sodium between the blood side and the dialysate side.

The fact is generally known that patients with high blood pressure are advised against eating table salt (NaCl). Blood pressure can be lowered, on the one hand, by a low-salt diet and, on the other hand, by an effective extraction of sodium during dialysis. To reduce the sodium content of the extracellular space during dialysis in order to achieve a lowering of blood pressure, it has been proposed to use a peritoneal dialysis solution with a low sodium content (Clin. Neph. Vol. 41 (6) (1994) pp. 357-363, Nakayama et al.). The peritoneal dialysis solution known from this publication has a sodium content of 120 mmol/l. Further components are calcium ions, magnesium ions (these cations are usually dispensed with chloride as the anion), lactate and glucose. The use of this peritoneal dialysis solution produces a significant reduction of the extracellular sodium content and of blood pressure, which is due to the fact that sodium ions are extracted to a substantial extent by diffusion and not by convective transport due to the increased concentration gradient.

The use of the previously known peritoneal dialysis solution, however, has some unwanted side-effects which are due, on the one hand, to a deficient dehydration of the patient and, on the other hand, to hyponatremia. In particular with patients with low oral sodium intake, the sole use of the said peritoneal dialysis solution with a sodium concentration of 120 mmol/l is associated with substantial disadvantages (hyponatremia) and is therefore unacceptable.

Peritoneal dialysis solutions are known from U.S. patent specifications U.S. Pat. No. 5,589,197, U.S. Pat. No. 5,629,025 and U.S. Pat. No. 5,631,025 which contain different osmotic agents and whose sodium content lies in the range between 35 and 125 mmol/l. A sodium ion concentration of ≤120 mmol/l is set forth as the preferred concentration range. A lowering of blood pressure and an increase in the ultrafiltration volume has likewise been found clinically with a peritoneal dialysis solution of this type with the same osmolarity with respect to already known standard solutions having typical sodium concentrations in the range of 134 mmol/l. However, the above-described clinical disadvantages due to too low a sodium content also result on the use of the peritoneal dialysis solutions known from the U.S. patent specifications.

The problem of high blood pressure (at a sodium ion concentration of approximately 134 mmol/l) or the problem that clinical side-effects are to be anticipated (at a sodium ion concentration ≤120 mmol/l) thus arises with already known peritoneal dialysis solutions. As a rule, a sodium ion concentration in the range of 134 mmol/l is set in the peritoneal dialysis usual today since in this manner the described side-effects of dialysis solutions with a low sodium content can be avoided. The simultaneously resulting problem of high blood pressure is treated by medication.

It is the object of the present invention to provide a solution for peritoneal dialysis which has a blood pressure-lowering effect and in which the side effects known by the use of peritoneal dialysis solutions with a low sodium content do not occur.

This object is satisfied by a solution for peritoneal dialysis having the features of claim 1. According to this, the sodium ion concentration of the peritoneal dialysis solution lies in a range from 121 to 129 mmol/l. In a preferred aspect of the invention, the sodium ion concentration of the solution lies in the range from 124 to 126 mmol/l. Particularly favorable results can be achieved with a peritoneal dialysis solution whose sodium ion concentration lies at 125 mmol/l. A peritoneal dialysis solution with a sodium content of 125 mmol/l is therefore particularly to be preferred.

Sodium is typically used in the form of table salt (NaCl), i.e. as a chloride. A reduction in the sodium ion concentration can therefore result in an equimolar reduction in the chloride ion concentration. A synergetic effect cannot be precluded due to the chloride ion concentration necessarily likewise lowered in the case of the use of sodium as the chloride.

The solution in accordance with the invention for peritoneal dialysis permits an effective lowering of blood pressure with the avoidance of side-effects, with these effects occurring at a sodium ion content in the claimed range and particularly pronouncedly at 125 mmol/l and preferably 91-94 mmol/l chloride ion content. It is equally possible to set the sodium ion concentration in a range between 126 and 129 mmol/l, for example at 127 mmol/l or at 128 mmol/l. Concentration values below the particularly preferred value of 125 mmol/l, i.e. 121, 122, 123 and 124 mmol/l, i.e. concentrations in the range 121-124 mmol/l are also conceivable. Adapted chloride ion concentrations are particularly to be preferred in this connection. The peritoneal dialysis solution in accordance with the invention results in an increase in salt excretion and serves to support the oral salt diet. Anti-hypertension agents can be dispensed with in more than 50% of the peritoneal dialysis patients due to the blood pressure-lowering effect of the solution in accordance with the invention.

In a further aspect of the invention, provision is made for the solution for peritoneal dialysis furthermore to comprise an osmotic agent, further electrolytes and a buffer.

It is known from EP 0 935 967 A2 to provide a peritoneal dialysis solution consisting of two separate solutions, with the first separate solution containing calcium ions, further electrolyte salts and glucose and being acidified to a pH below 3.2 using a physiologically compatible acid and with the second separate solution containing bicarbonate with a content of ≤10 mmol/l and the salt containing a weak acid with a pKa<5. A peritoneal dialysis solution of this type produces the advantage that, on the one hand, the degradation of glucose is prevented during the heat sterilization and that, on the other hand, no special demands have to be made on the pouch material with respect to the $CO_2$ barrier properties due to the low $CO_2$ partial pressure.

A solution for peritoneal dialysis of this type consisting of two separate solutions can also be considered for the present invention.

Provision can accordingly be made for the solution to consist of two separate solutions and for the first separate solution to comprise the osmotic agent and a physiologically compatible acid and for the second solution to comprise a buffer.

If the solution for peritoneal dialysis consists of two separate solutions, provision can be made for sodium ions to be present in each of the separate solutions. In this context, the mixing ratio is to be set such that the sodium ion concentration of the peritoneal dialysis solution, that is of the finished application solution, lies in the range between 121 and 129 mmol/l, preferably between 124 and 126 mmol/l and particularly preferably at 125 mmol/l.

In a further aspect of the present invention, provision is made for the peritoneal dialysis solution further to comprise calcium ions, magnesium ions, $H^+$ excess ions, chloride ions, lactate ions, hydrogen carbonate ions and glucose in addition to sodium ions.

If two separate solutions are used, provision can be made for further electrolytes, the osmotic agent (for example glucose) as well as a physiologically compatible acid to be present in a first separate solution in addition to calcium ions. The buffer system can be presented in a second separate solution. This can, for example, consist of bicarbonate and the salt of a weak acid (e.g. lactate). In accordance with the teaching of EP 0 935 967 A2, favorable results are achieved when the first separate solution is acidified to a pH below 3.2 and when the bicarbonate concentration of the second separate solution does not exceed 10 mmol/l. Reference is made to the content of EP 0 935 967 A2.

If the peritoneal dialysis solution consists of two separate solutions, provision can be made for the first separate solution to include the following components:

| | |
|---|---|
| Sodium ions [mmol/l]: | 172-200 |
| Calcium ions [mmol/l]: | 2-4 |
| Magnesium ions [mmol/l]: | 0.8-1.2 |
| $H^+$ excess ions [mmol/l]: | 0.9-1.1 |
| Chloride [mmol/l]: | 176-210 |
| Glucose [mmol/l]: | 100-500. |

The second separate solution can include the following components:

| | |
|---|---|
| Sodium ions [mmol/l]: | 70-80 |
| Lactate [mmol/l]: | 65-75 |
| Hydrogen carbonate [mmol/l]: | 4-6 |

The concentration range of the sodium ions of the application solution in accordance with the invention can easily be set by a suitable mixing ratio of the first and second separate solutions.

Other suitable buffer systems can also be considered in addition to the buffer system based on lactate and hydrogen carbonate. A purely bicarbonate buffered solution can be used, for example. Accordingly, in a further aspect of the invention, provision is made that the buffer consists of a hydrogen carbonate buffer. In this connection, provision can be made for the solution to consist of two separate solutions. The first separate solution can contain sodium ions, calcium ions, magnesium ions, $H^+$ excess ions, chloride ions and glucose and the second separate solution can contain sodium ions and hydrogen carbonate ions.

The first separate solution can be composed as follows:

| | |
|---|---|
| Sodium ions [mmol/l]: | 172-200 |
| Calcium ions [mmol/l]: | 2-4 |
| Magnesium ions [mmol/l]: | 0.8-1.2 |
| $H^+$ excess [mmol/l]: | 0.9-1.1 |
| Chloride [mmol/l]: | 176-210 |
| Glucose [mmol/l]: | 100-500 |

The second separate solution can contain the bicarbonate buffer and have the following composition:

| | |
|---|---|
| Sodium ions [mmol/l]: | 70-80 |
| Hydrogen carbonate [mmol/l]: | <80 |

If two separate solutions are used, they are typically heat sterilized, subsequently combined to form the application solution and then dispensed to the patient. Instead of two separate solutions, more than two can also be used provided this is meaningful in the individual case.

It is equally conceivable only to provide one separate solution and to present sodium ions in it in the concentration range in accordance with the invention.

The present invention furthermore relates to a double-chambered pouch having a solution in accordance with any one of the claims 1 to 5 which consists of a plastic pouch in which a first chamber with the first separate solution and a second chamber with the second separate solution are arranged adjacent to one another, with both chambers being separated by a weld seam dimensioned such that it opens on pressure on one of the chambers filled with liquid so that the content of the two chambers can be mixed with one another. In a double-chambered pouch of this type, the buffer system consisting, for example, of lactate and bicarbonate can be stored in a pouch chamber, while glucose and the electrolytes can be stored in a second chamber in an acid environment. After the sterilization, the pouch contents are mixed with one another and supplied to the patient. In this connection the sodium ion concentrations of the separate solutions are to be selected such that the sodium ion concentration in accordance with the invention results in the finished application solution.

Further details and advantages of the invention will be explained in more detail with reference to the embodiment shown in the following:

| | Phase II Study | | | | | |
|---|---|---|---|---|---|---|
| | CAPD low-sodium solution FME, 2003 | | | CAPD low-sodium solution Nakayama et al., 1994 | | |
| Time (weeks) | W 0 | W +2 | W +4 | W 0 | W +2 | W +4 |
| patients | N = 4 | N = 4 | N = 4 | N = 9 | N = 8 | N = 7 |
| D sodium (mmol/l) | 134 | 125 | 125 | 132 | 120 | 120 |
| D chloride (mmol/l) | 102.5 | 93.5 | 93.5 | 96 | 84 | 84 |
| MAD (mmHg) | 116 | 105 | 108 | 123 | 116 | 107 |
| KG (kg) | 65.5 | 65.5 | 64.8 | 61 | 61.7 | 61.6 |
| Average S sodium (mmol/l) | 138.8 | 135.5 | 137.0 | 137 | 133 | 136 |
| Average UF volume (ml/day) | 1088 | n.a. | 1068 | 918 | 880 | 890 |

-continued

| | Phase II Study | | | | |
|---|---|---|---|---|---|
| | CAPD low-sodium solution FME, 2003 | | CAPD low-sodium solution Nakayama et al., 1994 | | |
| Average TPN excretion (mmol/day) | 83.2 | n.a. | 55.1 | 38 | n.a. | 85 |
| SUE | | None | | 2× drop out: 1× hyponatremia, 1 hyperhydration | | |

Legend: FME, Fresenius Medical Care; W, week; N, number of patients; D, dialysate; S, serum; MAD, mean arterial (blood) pressure (formula: MAD = (SBD − DBD)/3 + DBD; SBD, systolic blood pressure; DBD, diastolic blood pressure; KG, body weight; UFV, ultrafiltration volume; TPNA, transperitoneal sodium excretion; SUE, serious unwanted event; n.a., not available.

The table shows the result of a study in which dialysis patients were treated with the peritoneal dialysis solution in accordance with the invention (columns 2-4). The results of the study which can be seen in Clin. Neph. Vol. 41(6) (1994) pp. 357-363, Nakayama et al. are set forth in comparison thereto (columns 5-7).

In the second line, the duration of treatment in weeks (W) and the number (N) of patients taking part at the respective time are set forth.

As results from the second and fifth columns, the patients were set to 134 mmol/sodium content at the start of the study with the dialysis solution (W 0) in accordance with the invention and to 132 mmol/l in the study of Nakayama et al. The chloride ion concentration of the peritoneal dialysis solution in accordance with the invention amounted to 93.5 mmol/l.

The sodium ion concentration in the dialysate was then set to 125 mmol/l in accordance with the present invention and compared with the published values of 120 mmol/l in accordance with Nakayama et al.

It can be seen from line 5 of the table that a clear reduction in the blood pressure (MAD) was able to be recorded on the use of the dialysis solution in accordance with the invention. After a treatment time of two weeks (W+2), a greater lowering of blood pressure resulted than with the comparison trial in accordance with Nakayama et al. both absolutely and relatively despite the higher sodium concentration of the dialysis solution in accordance with the invention. After a treatment time of four weeks, comparable blood pressure values as with the comparison trial resulted despite the higher sodium concentration of the solution in accordance with the invention.

The average ultrafiltration volume (UF volume) in the solution in accordance with the invention was at a similar order of magnitude as in the solution used at the start of the trial (134 mmol/l sodium content.

As results from the last line of the table, the application of the peritoneal dialysis solution in accordance with the invention results in no side-effects or in any serious unwanted incidents. In contrast to this, two patients had to abort the study in the trials in accordance with Nakayama et al. In one case, hyperhydration was found; in another case, the treatment was ended due to hyponatremia and the resulting side-effects.

The dialysis solution in accordance with the invention thus permits peritoneal dialysis in which the side-effects known from previously known dialysis solutions with a low sodium content can be avoided and in which simultaneously an effective lowering of blood pressure can be achieved.

The invention claimed is:

1. A set for use in peritoneal dialysis, the set comprising two separate solutions, a first separate solution and second separate solution, wherein the first separate solution includes an osmotic agent and a physiolocically compatible acid,
   wherein when the two separate solutions are mixed to form a mixed solution, the mixed solution contains sodium ions in a concentration in the range from 124 to 126 mmol/l and chloride ions in a concentration in the range from 91-94 mmol/l,
   wherein the first separate solution includes components in the following ranges:

| | |
|---|---|
| Sodium ions [mmol/l]: | 172-200 |
| Calcium ions [mmol/l]: | 2-4 |
| Magnesium ions [mmol/l]: | 0.8-1.2 |
| H$^+$ excess [mmol/l]: | 0.9-1.1 |
| Chloride [mmol/l]: | 176-210 |
| Glucose [mmol/l]: | 100-500. |

2. A set for use in peritoneal dialysis in accordance with claim 1, wherein the sodium ion concentration of the mixed solution is 125 mmol/l.

3. A set for use in peritoneal dialysis in accordance with claim 1, wherein sodium ions are present in each of the two separate solutions.

4. A set for use in peritoneal dialysis in accordance with claim 1, wherein the peritoneal dialysis solution further include calcium ions, magnesium ions, H+ excess ions, and wherein the osmotic agent is glucose.

5. A double chambered pouch comprising the set for use in peritoneal dialysis in accordance with claim 1, wherein the double chambered pouch consists of a plastic pouch in which a first chamber having the first separate solution and a second chamber having the second separate solution are arranged adjacent to one another, with the first chamber and the second chamber being separated by weld seam dimensioned such that the welded seam opens on pressure on one of the chambers filled with liquid so that the content of the two chambers can be mixed with one another.

\* \* \* \* \*